United States Patent
Gao et al.

(10) Patent No.: US 11,801,373 B1
(45) Date of Patent: Oct. 31, 2023

(54) INSOLUBLE TRANSDERMAL MICRONEEDLE PATCH, AND PREPARATION METHOD THEREFOR AND APPLICATION THEREOF

(71) Applicants: Technical Institute of Physics and Chemistry, CAS, Beijing (CN); Beijing CAS Microneedle Technology Ltd., Beijing (CN)

(72) Inventors: Yunhua Gao, Beijing (CN); Zequan Zhou, Beijing (CN); Suohui Zhang, Beijing (CN); Guozhong Yang, Beijing (CN)

(73) Assignees: TECHNICAL INSTITUTE OF PHYSICS AND CHEMISTRY, CAS, Beijing (CN); BEIJING CAS MICRONEEDLE TECHNOLOGY LTD., Beijing (CN)

( * ) Notice: Subject to any disclaimer, the term of this patent is extended or adjusted under 35 U.S.C. 154(b) by 0 days.

(21) Appl. No.: 18/329,399

(22) Filed: Jun. 5, 2023

Related U.S. Application Data (63) Continuation of application No. PCT/CN2022/113262, filed on Aug. 18, 2022.

(30) Foreign Application Priority Data

Sep. 14, 2021 (CN) .......................... 202111073707.1

(51) Int. Cl.
*A61M 37/00* (2006.01)
(52) U.S. Cl.
CPC . *A61M 37/0015* (2013.01); *A61M 2037/0023* (2013.01); *A61M 2037/0053* (2013.01); *A61M 2037/0061* (2013.01)

(58) Field of Classification Search
CPC ...... A61M 37/0015; A61M 2037/0023; A61M 2037/0053; A61M 2037/0061
See application file for complete search history.

(56) References Cited

FOREIGN PATENT DOCUMENTS

CN    113797155 A   * 12/2021

OTHER PUBLICATIONS

Zhou et al. (Asian Journal of Pharmaceutical Sciences 2021;16:612-622) (Year: 2021).*

(Continued)

*Primary Examiner* — Ernst V Arnold
(74) *Attorney, Agent, or Firm* — Zhigang Ma (57) ABSTRACT

An insoluble transdermal microneedle patch, includes microneedles and a backing. The microneedles include bases and needlepoints located on the base, and materials made for the microneedles include crosslinked sodium alginate. The backing is connected with the bases, and parts of the backing corresponding to the needlepoints are hollow portions. The microneedle patch can act in the skin for a long time, during it is used for transdermal delivery, drugs can enter skin micropores to be absorbed into a body through pores formed after swelled microneedles acting on the skin absorbs water, thereby increasing a bioavailability of the drugs during the transdermal delivery. After drug administration end, the microneedles are completely removed without increasing a metabolic burden in the body, soluble materials are prevented from being accumulated in the body, and the microneedles have good biological safety. A preparation method of the insoluble transdermal microneedle patch and application thereof are provided.

9 Claims, 3 Drawing Sheets

(56) References Cited

OTHER PUBLICATIONS

Google translation of CN113797155A 2021; 7 pages (Year: 2021).*
CNIPA, Notification of a First Office Action for CN202111073707.1, dated Feb. 1, 2023.
Technical Inst Physics & Chemistry Cas (Applicant), Reply to Notification of a First Office Action for CN202111073707.1, w/ (allowed) replacement claims, dated Apr. 13, 2023.
CNIPA, Notification to grant patent right for invention in CN202111073707.1, dated May 2, 2023.

* cited by examiner

INSOLUBLE TRANSDERMAL MICRONEEDLE PATCH, AND PREPARATION METHOD THEREFOR AND APPLICATION THEREOF

TECHNICAL FIELD

The disclosure relates to the field of medical technologies, and more particularly to an insoluble transdermal microneedle patch, a preparation method of the insoluble transdermal microneedle patch, and an application of the insoluble transdermal microneedle patch.

BACKGROUND

Transdermal delivery is a common method of administration, it can improve compliance of patients, avoid gastrointestinal drug decomposition, improve bioavailability, and eliminate pain caused by subcutaneous injection. An existence of stratum corneum limits a range of application for the transdermal delivery from molecular weight and water solubility of drugs, only a few drugs can perform administration through the transdermal delivery method, and an effect of the administration is limited. A research progress of the administration with microneedles is rapidly advanced with a development of micro-nanofabrication technology in recent years. Microneedle array is a minimal invasive device that can painlessly penetrate the stratum corneum of skin, assist the drugs penetrate a barrier during the transdermal delivery, and improve the bioavailability of the drugs. The microneedles have received widespread attention in recent years because of the advantages of mass production, low cost, numerous applicable drugs and patient autonomy in drug administration.

Researches of the microneedles are numerous, the microneedles can be divided into soluble microneedles and insoluble microneedles according to a solubility of the microneedles. It is necessary to research a metabolic and elimination method for components soluble in the skin before applying the soluble microneedles in clinical treatment, so as to judge biosafety of materials, thus a progress of commercialization will be inevitably delayed. The insoluble microneedles are mostly composed of a material such as metal, monocrystalline silicon, or macromolecule, the microneedles can be completely removed after being applied to the skin, without material accumulation in the body and reducing a burden of material metabolism. Therefore, the insoluble microneedles are mainly used in the clinical treatment at present. When the commonly used insoluble microneedles assist the transdermal delivery, it is necessary to apply drugs after the microneedles are removed, so as to make the drugs through skin pores formed by the microneedles. However, the skin pores begin to heal when the microneedles are removed, a retention time of the skin pores is limited by skin self-healing, and an overall efficiency of the transdermal delivery is difficult to be further developed.

SUMMARY

A first purpose of the disclosure is to provide an insoluble transdermal microneedle patch, the transdermal microneedle patch does not contain active substance, after applying drugs and removing the transdermal microneedle patch, a good bioavailability is obtained without applying drugs to promote absorption of the drugs.

A second purpose of the disclosure is to provide a preparation method of the insoluble transdermal microneedle patch.

A third purpose of the disclosure is to provide an application method of the insoluble transdermal microneedle patch.

In order to achieve the above first purpose, the disclosure provides the following technical solutions.

An insoluble transdermal microneedle patch, includes microneedles and a backing. Each of the microneedles includes a base and a needlepoint located on the base, and materials made for each of the microneedles mainly includes crosslinked sodium alginate. The backing is connected with the base, and parts of the backing corresponding to the needlepoints of the microneedles are hollow portions.

The base and the needlepoint of the transdermal microneedle patch can be formed as one whole or separately according to different technology. Moreover, the microneedle is composed of crosslinked sodium alginate, it can be understood that a main part of the microneedle is the crosslinked sodium alginate.

In an embodiment, the crosslinked sodium alginate is a structure crosslinked by sodium alginate and an in-situ crosslinker. The crosslinked sodium alginate obtained from this system as a main body of the microneedle not only has a higher strength, but also can be well applied to skin. Meanwhile, the crosslinked sodium alginate does not have irritation of the skin and it is safe and harmless. Moreover, the crosslinked sodium alginate has a higher swelling degree, it can effectively inject active substances into a subcutaneous area and has a higher bioavailability. Finally, the microneedles are insoluble in water and can be taken and stopped at any time during administration, so as to effectively control a dosage.

In an embodiment, the crosslinked sodium alginate is obtained by mixing an aqueous solution of the sodium alginate with an aqueous solution of the in-situ crosslinker into a uniform water solution and then crosslinking.

In an embodiment, the in-situ crosslinker is a mixed solution of calcium sodium edetate and gluconolactone, a mole ratio of the calcium sodium edetate and the gluconolactone is 1:0.8 to 1:1.2. Under this condition, the prepared microneedles have a higher strength and less skin irritation while ensuring a high swelling degree.

In an embodiment, a concentration of the calcium sodium edetate is 0.3-1.0 moles per liter (mol/L) in the aqueous solution of the in-situ crosslinker.

In an embodiment, a volume ratio of the aqueous solution of the sodium alginate and the aqueous solution of the in-situ crosslinker is 20:1-4:1.

In an embodiment, a solid content of the aqueous solution of the sodium alginate is 12-25%.

In an embodiment, a mole ratio of the gluconolactone and the calcium sodium edetate in the in-situ crosslinker is 0.8-1.2.

In an embodiment, the materials made for each of the microneedles include a pore-forming agent. An existence of the pore-forming agent contributes to intradermal water molecules entering interiors of upper needlepoint matrixes, thus regulating a drug release rate.

In an embodiment, an additive amount of the pore-forming agent accounts for 0.1-10 weight (wt) % of a total weight of the microneedle.

In an embodiment, the pore-forming agent is one or more selected from the group consisting of sodium chloride, sodium carbonate, sodium bicarbonate, ammonium bicarbonate, polyvinylpyrrolidone, hyaluronic acid and sodium hyaluronate, cellulose derivatives, trehalose, maltose, cyclodextrins.

In an embodiment, the backing is a backing film. A selection of the backing film is based on its ability to bind well with the base of the microneedle.

In order to achieve the above second purpose, the disclosure provides the following technical solutions.

A preparation method of the insoluble transdermal microneedle patch, includes the following steps:

mixing the aqueous solution of the sodium alginate with the aqueous solution of the in-situ crosslinker to form a uniform mixed solution;

placing the mixed solution on a microneedle mold and vacuumizing to make the mixed solution fill needle holes of the microneedle mold and complete sodium alginate crosslinking, and drying to obtain the microneedles; and removing the microneedles from the mold and connecting the base with the backing.

In an embodiment, the drying is blow drying, and a time of drying is 20-40 minutes (min).

In an embodiment, during liquid injection molding, a time of vacuumizing is 15-30 min based on a different additive amount of the in-situ crosslinker.

In order to achieve the above third purpose, the disclosure provides the following technical solutions.

An application method of the insoluble transdermal microneedle patch, includes: performing transdermal delivery by using the insoluble transdermal microneedle patch.

In an embodiment, the application method includes the following steps:

applying the microneedles of the transdermal microneedle patch onto human skin;

applying active substances to the microneedles by the hollow portions of the backing; and taking out the transdermal microneedle patch after completing administration.

In the disclosure, the active substance is one of drugs, medicated creams, medicated gels and the like. Specifically, the drugs can be divided into soluble drugs and insoluble drugs. The insoluble drugs can be lipophilic drugs such as tocopherol, antifungal/antibacterial drugs. The soluble drugs can be water-soluble acidic drugs such as L-ascorbic acid (e.g., vitamin C), water-soluble neutral drugs such as tranexamic acid, water-soluble alkaline drugs such as matrine, peptide drugs such as exenatide, polysaccharide drugs such as heparin, and nucleic acid drugs such as ribavirin.

Beneficial effects of the disclosure are as follows.

The insoluble transdermal microneedle patch provided in the disclosure can act in the skin for a long time, during it is used for transdermal delivery, drugs can enter skin micropores to be absorbed into a body through pores formed after swelled microneedles acting on the skin absorbs water, thereby increasing the bioavailability of the drugs during the transdermal delivery. After drug administration is ended, the microneedles may be completely removed without increasing a metabolic burden in the body, a soluble material is prevented from being accumulated in the body, and the microneedles have good biological safety.

BRIEF DESCRIPTION OF DRAWINGS

The following is a further detailed description of embodiments of the disclosure in conjunction with drawings.

DETAILED DESCRIPTION OF EMBODIMENTS

In order to describe the disclosure more clearly, the following will provide a further detailed description of the disclosure in conjunction with drawings and embodiments, similar components in the drawings are expressed by same reference numerals. Those skilled in the art should understand that the specific content described below is illustrative rather than restrictive and should not limit a scope of protection of the disclosure.

Embodiment 1

Figure 1:
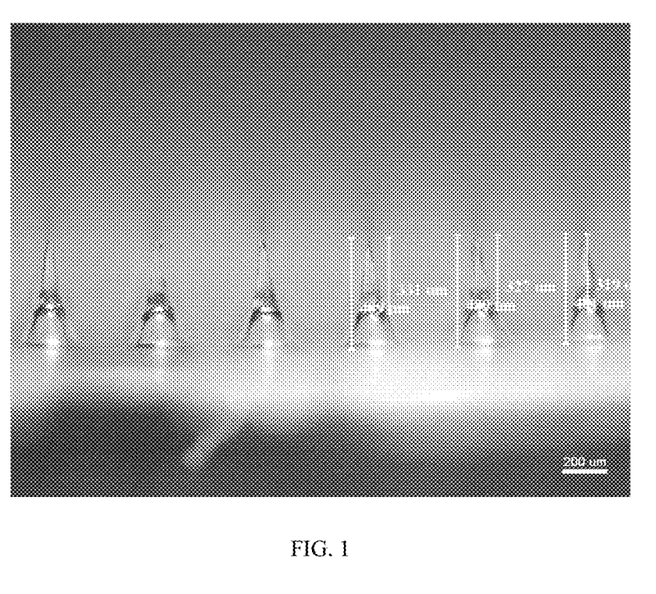
FIG. 1 illustrates a fluorescence microscope diagram of sodium alginate swelling microneedles according to an embodiment 1.
Figure 2:
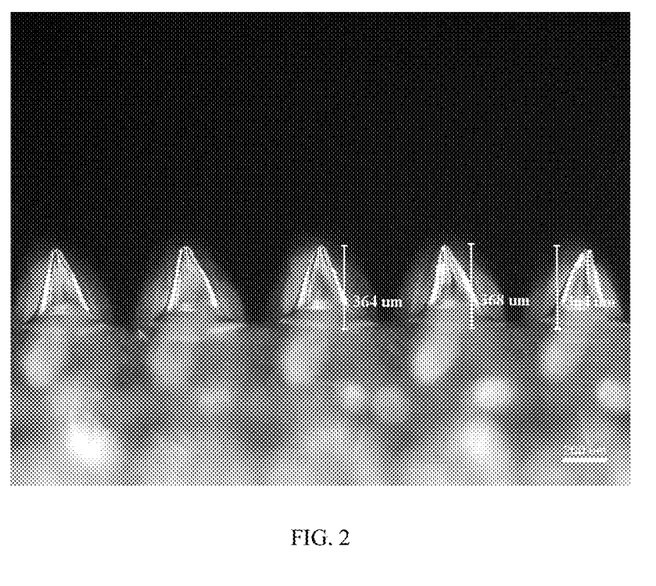
FIG. 2 illustrates a fluorescence microscope diagram of the sodium alginate swelling microneedles after absorbing water according to the embodiment 1.

According to data in Table 1, 1 gram (g) sodium alginate powder is weighed and dissolved in 9 milliliter (mL) ultrapure water as a sodium alginate solution (i.e., an aqueous solution of sodium alginate). 0.112 g calcium sodium edetate and 0.0534 g gluconolactone are weighted and dissolved in 1 mL ultrapure water as a crosslinked solution (i.e., an aqueous solution of in-situ crosslinker). The sodium alginate solution and the crosslinked solution are mixed to obtain a mixed solution, the mixed solution is spread on a microneedle mold, and a volume of the mixed solution added to each microneedle unit is 40 microliters (μL). The microneedle mold is vacuumed for 20 minutes (min), blown and dried for 30 min to obtain formed crosslinked sodium alginate microneedles, then the formed crosslinked sodium alginate microneedles are taken out, and backs of the formed crosslinked sodium alginate microneedles are attached with a backing film (i.e., backing) to obtain an insoluble transdermal microneedle patch. A fluorescence microscope diagram of the obtained microneedles is shown in FIG. 1, and a fluorescence microscope diagram of the obtained microneedles after water absorption and swelling is shown in FIG. 2. Thus, the microneedles after the water absorption can still keep complete shapes, and volumes of them become large.

Embodiment 2

According to data in Table 1, 1 g sodium alginate powder is weighed and dissolved in 9 mL ultrapure water as a sodium alginate solution. 0.224 g calcium sodium edetate and 0.125 g gluconolactone are weighted and dissolved in 1 mL ultrapure water as a crosslinked solution. The sodium alginate solution and the crosslinked solution are mixed to obtain a mixed solution, the mixed solution is spread on a microneedle mold, and a volume of the mixed solution added to each microneedle unit is 40 µL. The microneedle mold is vacuumed for 20 min, blown and dried for 30 min to obtain formed crosslinked sodium alginate microneedles, then the formed crosslinked sodium alginate microneedles are taken out, and backs of the formed crosslinked sodium alginate microneedles are attached with a backing film to obtain an insoluble transdermal microneedle patch.

Embodiment 3

According to data in Table 1, 1.5 g sodium alginate powder is weighed and dissolved in 8.5 mL ultrapure water as a sodium alginate solution. 0.281 g calcium sodium edetate and 0.133 g gluconolactone are weighted and dissolved in 1.5 mL ultrapure water as a crosslinked solution. The sodium alginate solution and the crosslinked solution are mixed to obtain a mixed solution, the mixed solution is spread on a microneedle mold, and a volume of the mixed solution added to each microneedle unit is 40 µL. The microneedle mold is vacuumed for 20 min, blown and dried for 30 min to obtain formed crosslinked sodium alginate microneedles, then the formed crosslinked sodium alginate microneedles are taken out, and backs of the formed crosslinked sodium alginate microneedles are attached with a backing film to obtain an insoluble transdermal microneedle patch.

Embodiment 4

According to data in Table 1, 1.5 g sodium alginate powder is weighed and dissolved in 8.5 mL ultrapure water as a sodium alginate solution. 0.393 g calcium sodium edetate and 0.214 g gluconolactone are weighted and dissolved in 1.5 mL ultrapure water as a crosslinked solution. The sodium alginate solution and the crosslinked solution are mixed to obtain a mixed solution, the mixed solution is spread on a microneedle mold, and a volume of the mixed solution added to each microneedle unit is 40 µL. The microneedle mold is vacuumed for 20 min, blown and dried for 30 min to obtain formed crosslinked sodium alginate microneedles, then the formed crosslinked sodium alginate microneedles are taken out, and backs of the formed crosslinked sodium alginate microneedles are attached with a backing film to obtain an insoluble transdermal microneedle patch.

Embodiment 5

According to data in Table 1, 2 g sodium alginate powder is weighed and dissolved in 8 mL ultrapure water as a sodium alginate solution. 0.449 g calcium sodium edetate and 0.214 g gluconolactone are weighted and dissolved in 2 mL ultrapure water as a crosslinked solution. The sodium alginate solution and the crosslinked solution are mixed to obtain a mixed solution, the mixed solution is spread on a microneedle mold, and a volume of the mixed solution added to each microneedle unit is 40 µL. The microneedle mold is vacuumed for 20 min, blown and dried for 30 min to obtain formed crosslinked sodium alginate microneedles, then the formed crosslinked sodium alginate microneedles are taken out, and backs of the formed crosslinked sodium alginate microneedles are attached with a backing film to obtain an insoluble transdermal microneedle patch.

Embodiment 6

According to data in Table 1, 2 g sodium alginate powder is weighed and dissolved in 8 mL ultrapure water as a sodium alginate solution. 0.598 g calcium sodium edetate and 0.285 g gluconolactone are weighted and dissolved in 2 mL ultrapure water as a crosslinked solution. The sodium alginate solution and the crosslinked solution are mixed to obtain a mixed solution, the mixed solution is spread on a microneedle mold, and a volume of the mixed solution added to each microneedle unit is 40 µL. The microneedle mold is vacuumed for 20 min, blown and dried for 30 min to obtain formed crosslinked sodium alginate microneedles, then the formed crosslinked sodium alginate microneedles are taken out, and backs of the formed crosslinked sodium alginate microneedles are attached with a backing film to obtain an insoluble transdermal microneedle patch.

Embodiment 7

According to data in Table 1, 1 g sodium alginate powder is weighed and dissolved in 9 mL ultrapure water as a sodium alginate solution. 0.561 g calcium sodium edetate and 0.267 g gluconolactone are weighted and dissolved in 2.5 mL ultrapure water as a crosslinked solution. The sodium alginate solution and the crosslinked solution are mixed to obtain a mixed solution, the mixed solution is spread on a microneedle mold, and a volume of the mixed solution added to each microneedle unit is 40 µL. The microneedle mold is vacuumed for 20 min, blown and dried for 30 min to obtain formed crosslinked sodium alginate microneedles, then the formed crosslinked sodium alginate microneedles are taken out, and backs of the formed crosslinked sodium alginate microneedles are attached with a backing film to obtain an insoluble transdermal microneedle patch.

Embodiment 8

According to data in Table 1, 1 g sodium alginate powder is weighed and dissolved in 9 mL ultrapure water as a sodium alginate solution. 0.748 g calcium sodium edetate and 0.356 g gluconolactone are weighted and dissolved in 2.5 mL ultrapure water as a crosslinked solution. The sodium alginate solution and the crosslinked solution are mixed to obtain a mixed solution, the mixed solution is spread on a microneedle mold, and a volume of the mixed solution added to each microneedle unit is 40 µL. The microneedle mold is vacuumed for 20 min, blown and dried for 30 min to obtain formed crosslinked sodium alginate microneedles, then the formed crosslinked sodium alginate microneedles are taken out, and backs of the formed crosslinked sodium alginate microneedles are attached with a backing film to obtain an insoluble transdermal microneedle patch.

TABLE 1

| Microneedle component | | Embodiment 1 | Embodiment 2 | Embodiment 3 | Embodiment 4 | Embodiment 5 | Embodiment 6 | Embodiment 7 | Embodiment 8 |
|---|---|---|---|---|---|---|---|---|---|
| Solid content of sodium alginate (%) | | 10 | 10 | 15 | 15 | 20 | 20 | 25 | 25 |
| Crosslinking solution | calcium sodium edetate (mol/L) | 0.3 | 0.6 | 0.5 | 0.7 | 0.6 | 0.8 | 0.6 | 0.8 |
| | gluconolactone (mol/L) | 0.3 | 0.7 | 0.5 | 0.8 | 0.6 | 0.5 | 0.6 | 0.8 |
| $V_{sodium\ alginate}:V_{crosslinking\ solution}$ | | 10:1 | 10:1 | 20:3 | 20:3 | 5:1 | 5:1 | 4:1 | 4:1 |

Where $V_{sodium\ alginate}$ represents a volume of sodium alginate, and $V_{crosslinking\ solution}$ represents a volume of crosslinking solution.

Comparative Embodiment 1

1 g sodium alginate powder is weighed and dissolved in 9 mL ultrapure water as a sodium alginate solution. 0.561 g calcium sodium edetate is weighed and dissolved in 2.5 mL ultrapure water as a crosslinked solution without gluconolactone. The sodium alginate solution and the crosslinked solution are mixed to obtain a mixed solution, the mixed solution is spread on a microneedle mold, and a volume of the mixed solution added to each microneedle unit is 40 μL. The microneedle mold is vacuumed for 20 min, blown and dried for 30 min to obtain formed crosslinked sodium alginate microneedles, then the formed crosslinked sodium alginate microneedles are taken out, and backs of the formed crosslinked sodium alginate microneedles are attached with a backing film.

Comparative Embodiment 2

1 g sodium alginate powder is weighed and dissolved in 9 mL ultrapure water as a sodium alginate solution. 0.438 g ethylenediamine tetraacetic acid and 0.267 g gluconolactone are weighted and dissolved in 2.5 mL ultrapure water as a crosslinked solution. The sodium alginate solution and the crosslinked solution are mixed to obtain a mixed solution, the mixed solution is spread on a microneedle mold, and a volume of the mixed solution added to each microneedle unit is 40 μL. The microneedle mold is vacuumed for 20 min, blown and dried for 30 min to obtain formed crosslinked sodium alginate microneedles, then the formed crosslinked sodium alginate microneedles are taken out, and backs of the formed crosslinked sodium alginate microneedles are attached with a backing film.

Comparative Embodiment 3

1 g sodium alginate powder is weighed and dissolved in 9 mL ultrapure water as a sodium alginate solution. 0.112 g calcium sodium edetate and 0.0267 g gluconolactone are weighted and dissolved in 1 mL ultrapure water as a crosslinked solution. A mole ratio of the calcium sodium edetate and the gluconolactone in the crosslinked solution is 1:0.5. The sodium alginate solution and the crosslinked solution are mixed to obtain a mixed solution, the mixed solution is spread on a microneedle mold, and a volume of the mixed solution added to each microneedle unit is 40 μL. The microneedle mold is vacuumed for 20 min, blown and dried for 30 min to obtain formed crosslinked sodium alginate microneedles, then the formed crosslinked sodium alginate microneedles are taken out, and backs of the formed crosslinked sodium alginate microneedles are attached with a backing film.

Comparative Embodiment 4

1 g sodium alginate powder is weighed and dissolved in 9 mL ultrapure water as a sodium alginate solution. 0.561 g calcium sodium edetate and 0.401 g gluconolactone are weighted and dissolved in 2.5 mL ultrapure water as a crosslinked solution. A mole ratio of the calcium sodium edetate and the gluconolactone in the crosslinked solution is 1:1.5. The sodium alginate solution and the crosslinked solution are mixed to obtain a mixed solution, the mixed solution is spread on a microneedle mold, and a volume of the mixed solution added to each microneedle unit is 40 μL. The microneedle mold is vacuumed for 20 min, blown and dried for 30 min to obtain formed crosslinked sodium alginate microneedles, then the formed crosslinked sodium alginate microneedles are taken out, and backs of the formed crosslinked sodium alginate microneedles are attached with a backing film. The mixed solution of the sodium alginate solution and the crosslinked solution cannot keep a stable and uniform viscosity during a process of producing microneedles, and a solution volume of the microneedle unit is caused inaccurate. The microneedles produced contain undissolved calcium sodium edetate and gluconolactone particles visible to the naked eye.

Swelling Degree Test

Swelling microneedles from embodiments 1-8 are dried to a constant weight, and a mass of the swelling microneedles is determined as m1, then the swelling microneedles are soaked in pure water in a 37 centigrade (° C.) incubator until the mass remains constant, then they are taken out, wiped off surface moisture and weighted, the mass is recorded as m2, a swelling rate of hydrogel is calculated according to the following formula :

$SR=(m2-m1)/m1\times 100$

Skin Irritation Test

Test animal is a New Zealand white rabbit weighing 2.5 kilogram (kg).

Test samples are as follows. 4 samples are selected from patches of each embodiment, and each of the samples is cut into discs with a diameter of 2 centimeter (cm).

Test methods are as follows. The relevant provisions and contents of the "Technical Guidelines for the Study of Irritability, Allergy, and Hemolysis of Chemical Drugs"

issued by the National Food and Drug Administration are adopted. The patches are stuck on one side of back of the white rabbit, and torn off after 7 days. The skin irritations of the patches are evaluated by obtained averaging scores according to the following grading scale: (1) 0-0.49 is non-irritating; (2) 0.5-2.99 is mildly irritating; (3) 3.0-5.99 is moderately irritating; (4) 6.0-8.00 is strongly irritating, and results are listed in Table 2.

TABLE 2

Testing results of the embodiments 1-8.

| | Swelling degree (%) | Skin irritation |
|---|---|---|
| Embodiment 1 | 159.80 | 0.25 (Non-irritating) |
| Embodiment 2 | 137.57 | 0.25 (Non-irritating) |
| Embodiment 3 | 146.49 | 0.25 (Non-irritating) |
| Embodiment 4 | 111.04 | 0.25 (Non-irritating) |
| Embodiment 5 | 117.32 | 0.25 (Non-irritating) |
| Embodiment 6 | 109.19 | 0.5 (Mildly irritating) |
| Embodiment 7 | 114.16 | 0.25 (Non-Irritating) |
| Embodiment 8 | 105.68 | 0.25 (Non-irritating) |
| Comparative embodiment 1 | 0 (Dissolution) | 0.25 (Non-irritating) |
| Comparative embodiment 2 | 0 (Dissolution) | 0.25 (Non-irritating) |
| Comparative embodiment 3 | 0 (Disintegration) | 0.25 (Non-irritating) |
| Comparative embodiment 4 | 135.29 (Disintegration) | 1.5 (Mildly irritating) |

The dissolution refers to a uniform phase formed between microneedles and water. The disintegration refers to the microneedles being dispersed into multiple parts in water, without forming a uniform phase with water.

Drug Transdermal Permeability Test

Figure 3:
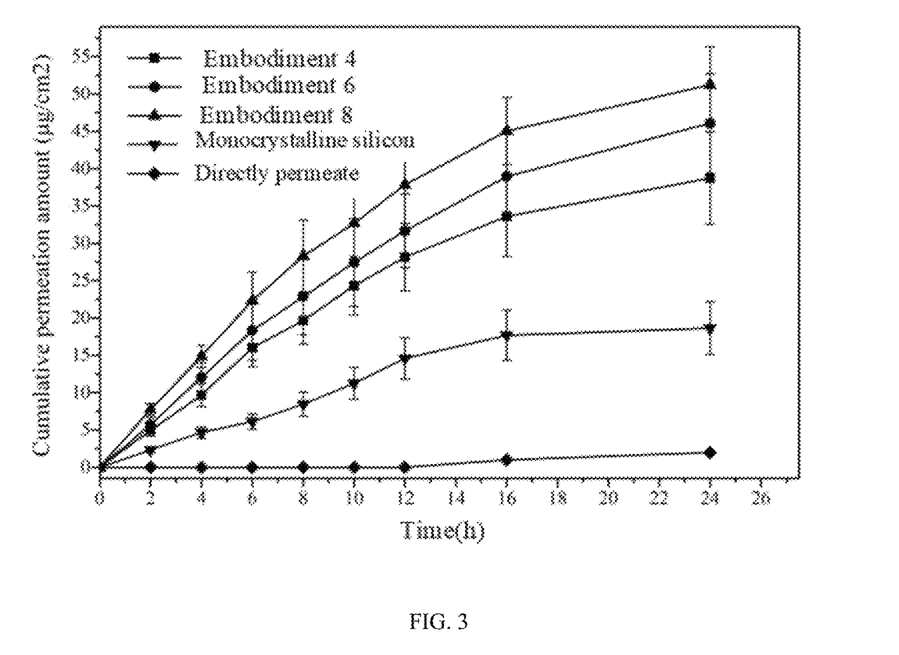
FIG. 3 illustrates a schematic diagram of transdermal permeation curves of the sodium alginate swelling microneedles assisted permeation of L-ascorbic acid according to an embodiment 4, an embodiment 6, and an embodiment 8.
Figure 4:
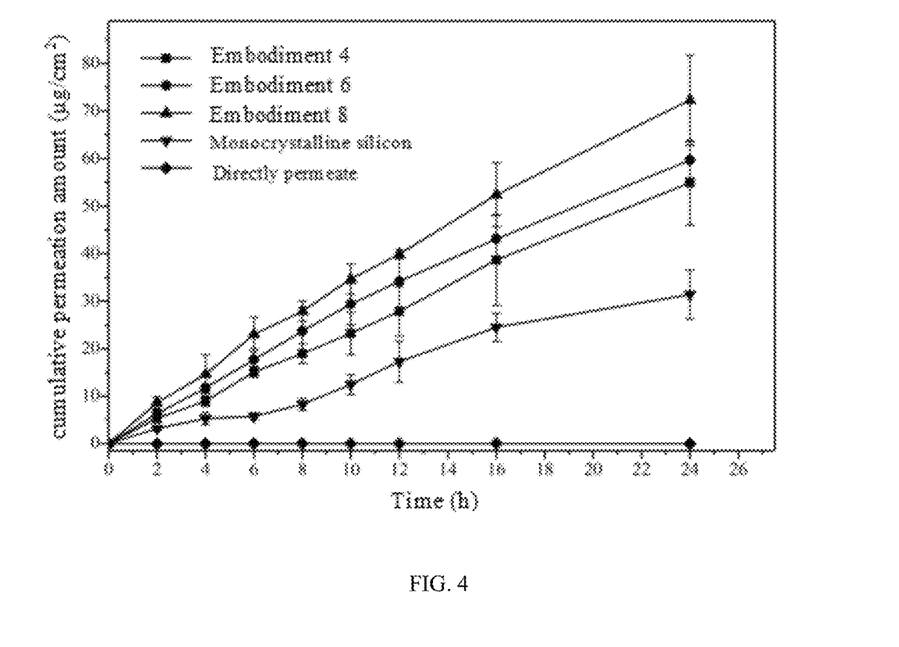
FIG. 4 illustrates a schematic diagram of transdermal permeation curves of the sodium alginate swelling microneedles assisted permeation of tranexamic acid according to the embodiment 4, the embodiment 6, and the embodiment 8.
Figure 5:
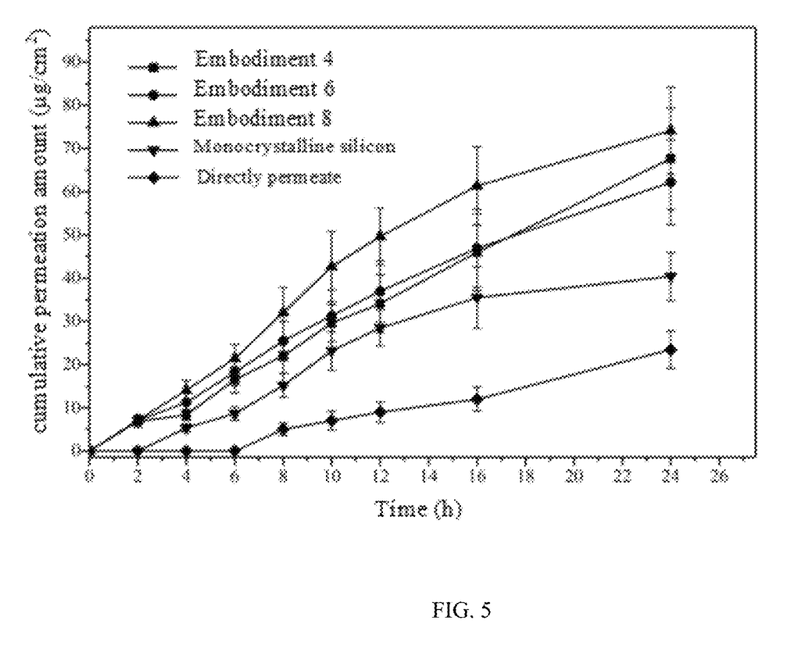
FIG. 5 illustrates a schematic diagram of transdermal permeation curves of the sodium alginate swelling microneedles assisted permeation of matrine according to the embodiment 4, the embodiment 6, and the embodiment 8.

A device used is the SYSTEM 912-24 fully automatic transdermal diffusion sampling system from Lugen Company in the United States. An effective transmission area of transdermal cups used is 0.625 square centimeter (cm$^2$). Skin used is fresh 800 micron (μm) thick pig ear skin. The crosslinked sodium alginate microneedles of each embodiment are applied to one side of stratum corneum of the skin, and dermis is facing a receiving pool. A volume of the receiving pool is 2.7 mL, and the microneedle patches obtained from each embodiment are conducted in-vitro percutaneous permeability test. Embodiment 4, embodiment 6 and embodiment 8 are conducted in-vitro percutaneous permeability test, control groups include skin treated with monocrystalline silicon puncture and untreated skin. L-ascorbic acid, tranexamic acid and matrine are individually selected as a transdermal drug. The skin treated with monocrystalline silicon puncture and the untreated skin are used as the control groups. Curve drawing results are shown in FIG. 3, FIG. 4 and FIG. 5. When the crosslinked sodium alginate microneedles are used as auxiliary permeation of the L-ascorbic acid, a cumulative permeation amount of the L-ascorbic acid is 2.74-2.08 times of that of the control group of the monocrystalline silicon microneedles, and the untreated skin without permeation. When the crosslinked sodium alginate microneedles are used as auxiliary permeation of the tranexamic acid, a cumulative permeation amount of the tranexamic acid is 2.35-1.75 times of that of the control group of the monocrystalline silicon microneedles, and the untreated skin without permeation. When the crosslinked sodium alginate microneedles are used as auxiliary permeation of the matrine, a cumulative permeation amount of the matrine is 1.83-1.5 times that of the control group of the monocrystalline silicon microneedles, and compared with the untreated skin control group, it increased by 3.16-2.68 times.

24-hour cumulative percutaneous permeabilities of the embodiments 1-8 are shown in Table 3.

TABLE 3

24-hour cumulative percutaneous permeabilities of the embodiments 1-8.

| | L-ascorbic acid (%) | Tranexamic acid (%) | Matrine (%) |
|---|---|---|---|
| Embodiment 1 | 23.1 | 43.5 | 50.3 |
| Embodiment 2 | 26.6 | 47.8 | 55.5 |
| Embodiment 3 | 30.8 | 49.3 | 65.3 |
| Embodiment 4 | 37.6 | 55.1 | 68.1 |
| Embodiment 5 | 43.4 | 55.3 | 65.6 |
| Embodiment 6 | 46.1 | 59.2 | 61.7 |
| Embodiment 7 | 55.4 | 65.2 | 73.5 |
| Embodiment 8 | 51.5 | 71.6 | 74.7 |
| Monocrystalline silicon | 17.6 | 32.1 | 40.6 |
| Directly permeate | 1.3 | 0 | 13.2 |

Obviously, the above embodiments of the disclosure are merely for the purpose of clearly describing the embodiments provided by the disclosure, rather than limiting the implementation methods of the disclosure. For those skilled in the art, on the basis of the above description, other different forms of modifications or changes can be made, and it is not possible to exhaustive list all the implementation methods here, any obvious changes or variations arising from the technical solution of the disclosure are still within a scope of protection of the disclosure.

What is claimed is:

1. An insoluble transdermal microneedle patch, comprising:
   microneedles, wherein each of the microneedles comprises a base and a needlepoint located on the base, and materials made for each of the microneedles comprise crosslinked sodium alginate; and
   a backing, connected with the base, wherein parts of the backing corresponding to the needlepoints of the microneedles are hollow portions;
   wherein the crosslinked sodium alginate is obtained by mixing an aqueous solution of sodium alginate with an aqueous solution of an in-situ crosslinker into a uniform water solution and then crosslinking;
   wherein the in-situ crosslinker is a mixed solution of calcium sodium edetate and gluconolactone, a mole ratio of the calcium sodium edetate and the gluconolactone is 1:0.8 to 1:1. 2;
   wherein a concentration of the calcium sodium edetate is 0.3-1.0 moles per liter (mol/L) in the aqueous solution of the in-situ crosslinker.

2. The insoluble transdermal microneedle patch as claimed in claim 1, wherein a volume ratio of the aqueous solution of the sodium alginate and the aqueous solution of the in-situ crosslinker is 20:1 to 4:1.

3. The insoluble transdermal microneedle patch as claimed in claim 1, wherein a solid content of the aqueous solution of the sodium alginate is 12-25%.

4. The insoluble transdermal microneedle patch as claimed in claim 1, wherein the materials made for each of the microneedles comprise a pore-forming agent.

5. The insoluble transdermal microneedle patch as claimed in claim 4, wherein an additive amount of the pore-forming agent accounts for 0.1-10 weight (wt) % of a total weight of the microneedle.

6. The insoluble transdermal microneedle patch as claimed in claim 4, wherein the pore-forming agent is one or more selected from the group consisting of sodium chloride, sodium carbonate, sodium bicarbonate, ammonium bicarbonate, polyvinylpyrrolidone, hyaluronic acid and sodium hyaluronate, trehalose, maltose, cyclodextrin.

7. A preparation method of the insoluble transdermal microneedle patch as claimed in claim 1, comprising the following steps:
   mixing the aqueous solution of the sodium alginate with the aqueous solution of the in-situ crosslinker to form a uniform mixed solution;
   placing the mixed solution on a microneedle mold and vacuumizing to make the mixed solution fill needle holes of the microneedle mold and complete sodium alginate crosslinking, and drying to obtain the microneedles;
   removing the microneedles from the mold and connecting the base with the backing.

8. An application method of the insoluble transdermal microneedle patch as claimed in claim 1, comprising: performing transdermal delivery by using the insoluble transdermal microneedle patch.

9. The application method as claimed in claim 8, comprising the following steps:
   applying the microneedles of the transdermal microneedle patch onto human skin;
   applying active substances to the microneedles by the hollow portions of the backing; and
   taking out the transdermal microneedle patch after completing administration.

* * * * *